United States Patent [19]

Markovitz et al.

[11] Patent Number: 5,302,977
[45] Date of Patent: Apr. 12, 1994

[54] EYEWEAR HAVING SELF-ADJUSTING EAR STEMS

[75] Inventors: Aaron M. Markovitz; Jeffrey K. Raub, both of Rochester, N.Y.

[73] Assignee: Bausch & Lomb Incorporated, Rochester, N.Y.

[21] Appl. No.: 966,239

[22] Filed: Oct. 26, 1992

[51] Int. Cl.⁵ .......................... G02C 5/06; G02C 5/16; G02C 5/20
[52] U.S. Cl. ...................... 351/114; 351/118; 351/123; 351/126; 2/426; 2/446; 2/448; 2/450
[58] Field of Search ................. 351/63, 83, 94, 95, 351/111, 114, 118, 123, 126, 150, 156; 2/423, 426, 439, 445, 446, 448, 450

[56] References Cited

U.S. PATENT DOCUMENTS

| | | | |
|---|---|---|---|
| 714,664 | 12/1902 | Briggs | 351/114 |
| 836,796 | 11/1906 | Anderson | |
| 1,968,193 | 7/1934 | Einson | 351/44 |
| 3,791,721 | 2/1974 | Helfrich | 351/156 |
| 4,202,609 | 5/1980 | Reese | 351/111 |
| 4,461,549 | 7/1984 | Reese et al. | 351/153 |
| 4,687,306 | 8/1987 | Lipson et al. | 351/83 |
| 4,723,844 | 2/1988 | Medina | 351/111 |
| 4,953,967 | 9/1990 | Somerville | 351/156 |

FOREIGN PATENT DOCUMENTS

| | | | |
|---|---|---|---|
| 860633 | 1/1971 | Canada | 88/36 |
| 0066914 | 4/1983 | Japan | 351/83 |

*Primary Examiner*—Bruce Y. Arnold
*Assistant Examiner*—R. D. Shafer
*Attorney, Agent, or Firm*—Salvatore P. Pace; Denis A. Polyn

[57] ABSTRACT

Eyewear, such as sunglasses, is provided having a self-adjusting ear stem system. The eyewear has upper and lower frame members which contain an elastic cord means disposed there through wherein the elastic cord means can be extended on opposite sides of the wearer's face to fit around the wearer's ears.

18 Claims, 4 Drawing Sheets

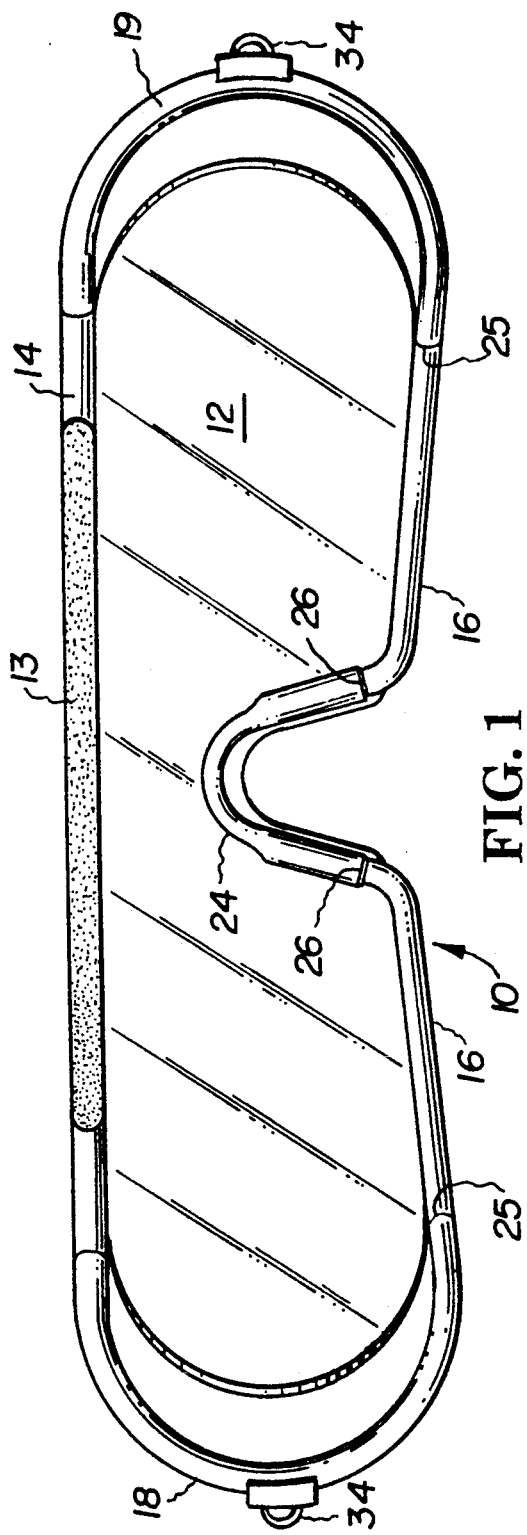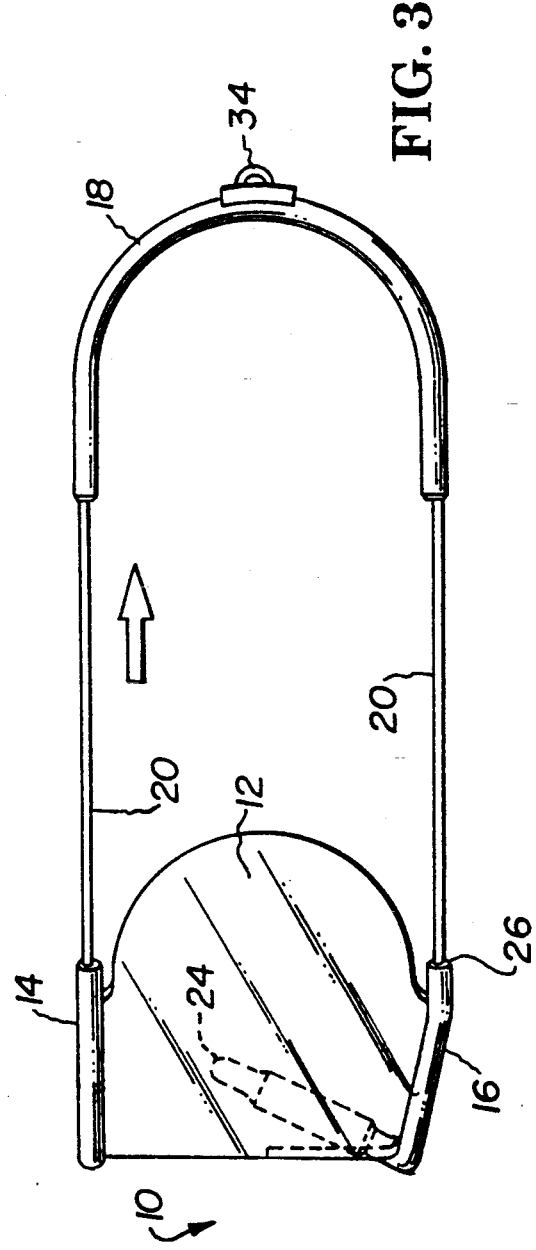

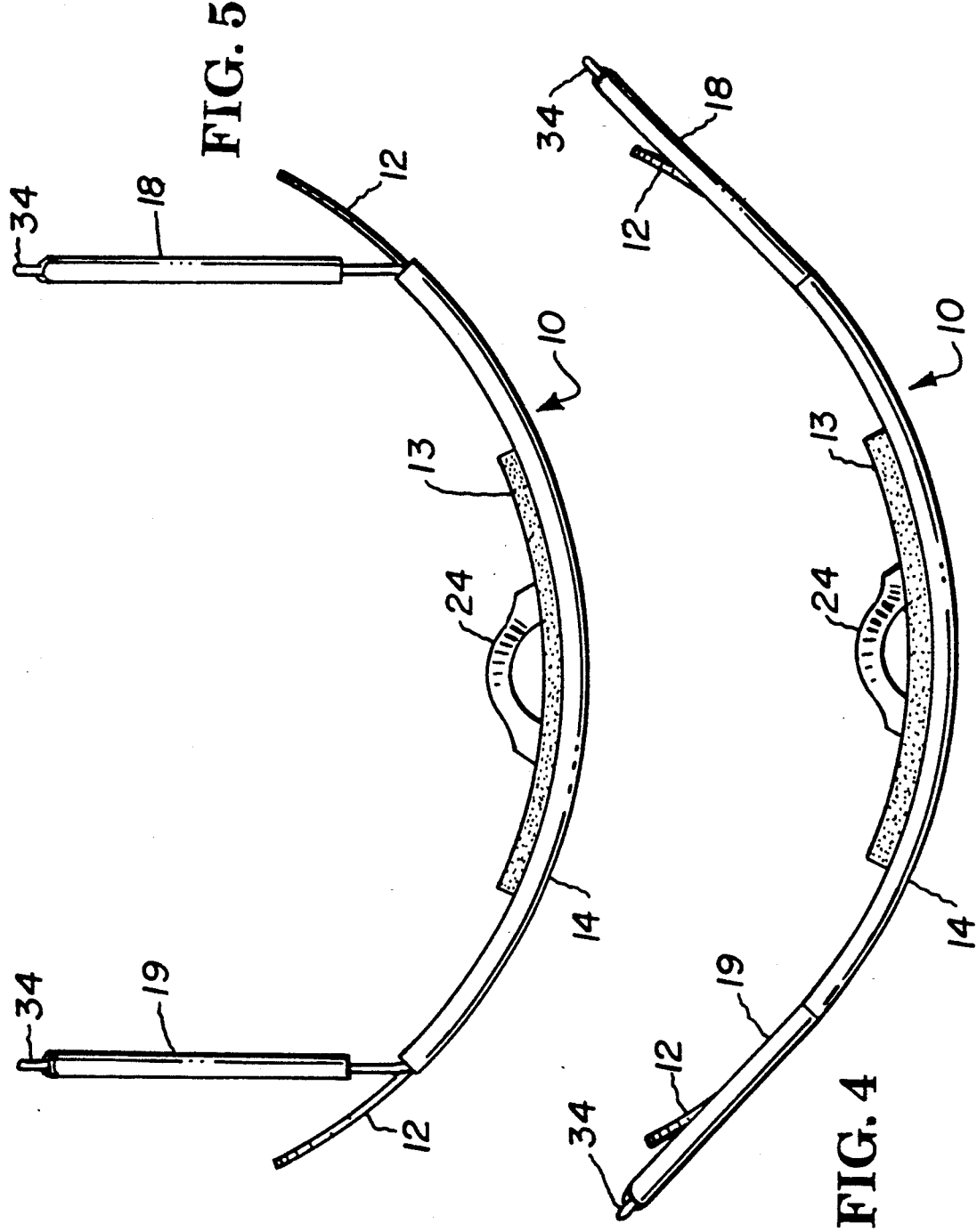

EYEWEAR HAVING SELF-ADJUSTING EAR STEMS

BACKGROUND OF THE INVENTION

1. Field of the Invention

The present invention relates to eyewear and, more particularly, to eyewear having a self-adjusting ear stem system.

2. Description of the Art

There are many varieties of wrap-around or shield-type eyewear, particularly sunglasses, available and known today. Generally, these sunglasses have cylindrical or spherical shaped lenses designed for use during sports activities. For example, these sunglasses are typically designed to fit firmly on the wearer's head during activities such as skiing, biking, speed skating, volleyball, and the like. In such applications, it is important that these sunglasses fit comfortably on the wearer's head yet have sufficient retention so as not to slip or fall off during active movement.

Conventional eyewear of this type, generally includes a one-piece lens that is supported by an upper frame member, a lower frame member, or a continuous frame member which surrounds the lens. The frame member or the lens is typically connected to two ear stems on opposite sides of the lenses. The ear stems are affixed to the frame members with hinges in a manner well known in the art. Most commonly, these sunglasses have conventional ear stems with a paddle shaped or an arcuate shaped end and are attached to the lens or frame members with conventional hinge means.

Other types of eyewear or eyeglasses have also been designed where the typical rigid ear stem is replaced with a flexible ear stem or suspension wires. Various rubber-like or plastic boots, which are attached to the free end of conventional ear stems, have also been designed to aid in the retention of the eyewear about the wearer's head. Last, retractable or spring-loaded hinges have also been designed which aid in the retention and fit of the eyewear.

However, none of these previous attempts to improve the retention of eyewear on the wearer's head, provide the secure retention necessary for active movement, comfortably fit the wearer's head, and have the means for self adjustment.

The present invention provides a new and unique ear stem system for maintaining the eyewear, and lenses, about the wearer's head. Further, this invention provides for a unique system which firmly attaches the eyewear to the wearer's face and self-adjusts to maintain uniform and constant pressure across the wearer's face or readjust after contact. Moreover, the present invention provides for a self-adjusting ear stem system wherein one size can comfortably fit a great cross section of people without providing complicated parts which require time-consuming adjustment procedures.

SUMMARY OF THE INVENTION

In accordance with the present invention, eyewear is provided having a self-adjusting ear stem system comprising a lens member containing at least one lens and having a top, and a bottom, an upper frame member substantially conforming to said top of said lens system, a lower frame member substantially conforming to said bottom of said lens system and containing two inner ends on opposite sides of the wearer's nose, and elastic means moveably connected to said upper and lower frame members and affixed at one or more locations on said top frame member or said lower frame member, and wherein said elastic means can be extended on opposite sides of said upper and lower frame members to fit around the wearer's ears.

BRIEF DESCRIPTION OF DRAWINGS

FIG. 1 is a rear view of one embodiment of the present invention;

FIG. 3 is a side view of the embodiment of FIG. 1 showing the ear stem system in an extended position;

FIG. 4 is a top view of the embodiment of FIG. 1 showing the ear stem system in a rest position;

FIG. 5 is a top view of the embodiment of FIG. 1 showing the ear stem system in an extended position;

DETAILED DESCRIPTION OF THE INVENTION

Figure 2:
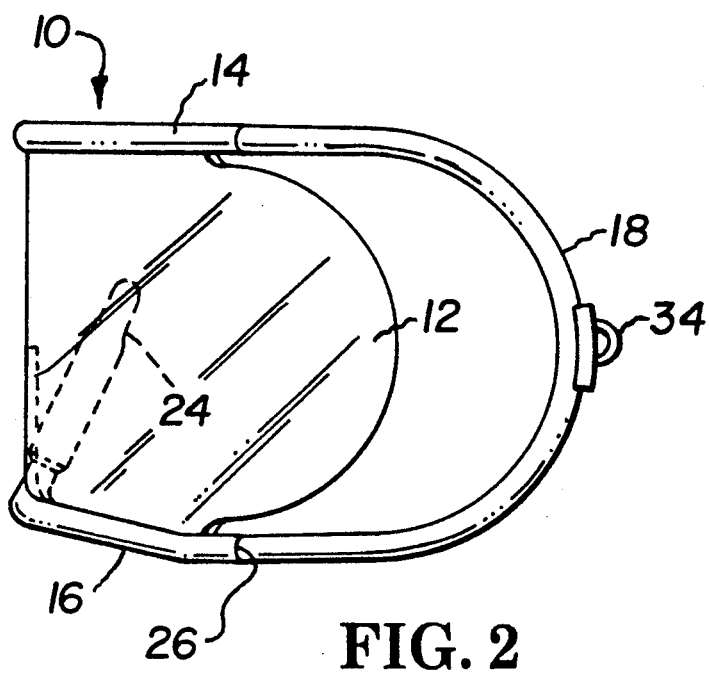
FIG. 2 is a side view of the embodiment of FIG. 1 showing the ear stem system in a rest position.

Referring to FIG. 1, eyewear 10 is shown comprising a curved lens 12, upper frame member 14 and lower frame member 16, and a pair of ear engaging members 18 and 19. Brow pad 13 is affixed to upper frame member 14 and positioned so as to come in contact with the wearer's forehead. Optionally, face pads (not shown) can also be affixed to the lower frame member 16 and positioned so as to come in contact with the wearer's cheeks. Upper frame member 14 conforms to the upper edge of lens 12 and lower frame member 16 has outer ends 25 and inner ends 26 which conform to the bottom edge of the left and right side of lens 12. Although lower frame member 16 is described herein as one member, it is preferably two separate members with outer ends 25 located near the side of the wearer's head and inner ends 26 located on opposite side of the wearer's nose.

An elastic cord 20 is slideably disposed within said upper frame member 14, lower frame member 16 and ear engaging members 18 and 19. The elastic cord 20 is secured at its ends to the inner ends 26 of frame member 16. Flexible bridge member 24 is slideably disposed over the inner ends 26 of lower frame member 16.

Figure 6:
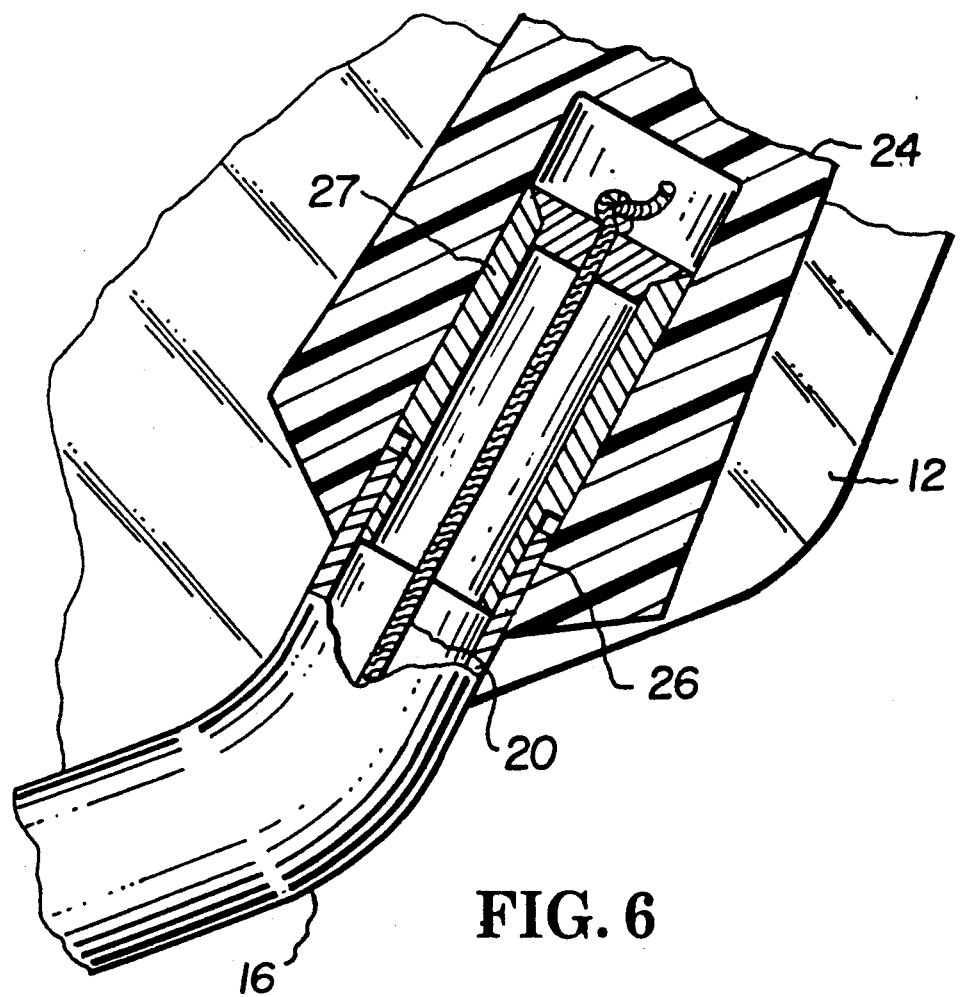
FIG. 6 is an enlarged sectional view of the nasal area of the embodiment of FIG. 1.

The ends of elastic cord 20 is affixed to inner ends 26 of lower frame member 16 with any conventional means such as a knot or with a suitable mechanical fastener. In a preferred embodiment as shown in FIG. 6, the ends of elastic cord 20 are affixed to pistons 27 which can move vertically in cooperation with inner ends 26 of lower frame member 16. As further shown in FIG. 6 which is an enlarged sectional view of one side of the nasal area of eyewear 10, elastic cord 20 is placed through an opening in piston 27 and secured with a knot. Other means for securing elastic cord 20 to piston 27 can be employed. Piston 27 partially fits inside of inner end 26 in a male-female connection and can slide vertically away from inner end 26. Flexible bridge member 24 is disposed over piston 26 (on both sides of the wearer's nose) and is in movable contact with inner ends 26.

According to this embodiment, flexible bridge member 24 can be affixed to pistons 27 allowing the vertical movement of pistons 27 to be transferred to flexible bridge member 24. In this manner, flexible bridge member 24 can remain substantially stationary on the wearer's nose even though eyewear 10 is violently moved or jarred such as from contact with a ball or other object. After movement, the present ear stem system self-adjusts to return the eyewear 10 to its normal position on the wearer's face. This embodiment allows the eyewear to "float" on the wearer's head while pistons 27 equalize the movement of the eyewear 10.

As evident to those skilled in the art, the elastic cord 20 can be any material having suitable elasticity and durability. Illustrative examples of such materials include elastomers made from known natural or synthetic polymeric materials such as nitrile rubbers, butyl rubbers, polyurethane rubbers, silicone rubbers, and the like. Various suitable fabrics or weaved materials can also be employed. Further, although the present invention does not require ear engaging members since the elastic cord or elastomer can itself be used, ear engaging members 18 and 19 can be employed of various design configurations for additional comfort. Ear engaging members 18 and 19 are preferably a soft material such as a flexible plastic or fabric material which helps to reduce the pull of the elastic cord 20 around the wearer's ear. There are virtually no limitations on the designs or materials that can be used for this purpose. Ear engaging members 18 and 19 as shown in the embodiment of FIG. 1, are designed to partially fit into frame members 14 and 16 which entirely hide elastic cord 20 when in the stored or rest position.

Frame members 14 and 16 can also be made of varying materials but are preferably made from conventional plastic materials used in eyewear frames such as cellulose acetate, nylon and the like, or light weight metal materials such as aluminum, aluminum alloys, titanium, titanium alloys and the like. Most preferred are the metal materials. Although the elastic cord 20 need only be in slideable or movable connection with frame members 14 and 16, it is preferred that frame members 14 and 16 define a tube whereby elastic cord 20 is freely slideable there through. In this manner, elastic cord 20 is continuously self-adjusting the pressure and fit of eyewear 10 and lens 12 on the wearer's face. The movement of elastic cord 20 through frame members 14 and 16 provides for a continuous and consistent pressure on the wearer's face and minimizes the movement of eyewear 10 and lens 12 during sports activities.

Frame members 14 and 16 can be affixed to lens 12 by any mechanical means. For example, lens 12 can have projections or tabs which are inserted into slots in frame members 14 and 16 and permanently affixed through the use of a friction connection or a suitable adhesive. Conventional fastening means suitable for the materials employed can also be used such as screws or rivets. The manner in which the frame members 14 and 16 are affixed to the lens 12 is not critical provided that the means for connecting the lens 12 to frame members 14 and 16 does not substantially interfere with the movement of elastic cord 20.

The lens 12 can be made of any conventional material used in sunglass or ophthalmic lenses such as glass and plastic but is preferably a suitable polycarbonate or similar plastic material. Moreover, while FIG. 1 embodies a single, unitary lens, a lens system can be employed wherein two lenses are connected in a manner which substantially resemble a single unitary lens. Further, the overall lens (or lens system) shape can vary but is preferably cylindrical, spherical, or toroidal, as is generally known in the art.

FIG. 2 shows a side view of the sunglasses shown in FIG. 1 and FIG. 4 shows a top view of the sunglasses shown in FIG. 1. In both FIG. 2 and FIG. 4, the ear stem system is in the rest or normal position. As best shown in FIG. 2, ear engaging member 18 has connecting means 34. Connecting means 34 can be used for attachment of a string or elastic strap if desired. Ear engaging members 18 and 19 can be pulled back stretching or extending elastic cord 20 for placement around the wearer's ear as shown in FIG. 3. After the ear engaging members are placed around the back of the wearer's ear, elastic cord 20 will move back towards its normal or rest position placing frame members 14 and 16 and lens 12 at a firm position on the wearer's face. Since elastic cord 20 moves freely through upper frame member 14 and lower frame member 16, the present invention can self adjust the tension about the wearer's face to provide a uniform and comfortable pressure at positions both above and below the wearer's eyes.

Frame members 14 and 16 can also have means for engaging and locking elastic cord 20, such as a recess or slit (not shown), in order to loosen the tension on elastic cord 20 in the areas between the frame members and the wearer's ear. This allows for the wearer to release the tension on the wearer's head during rest or normal wear.

Figure 7:
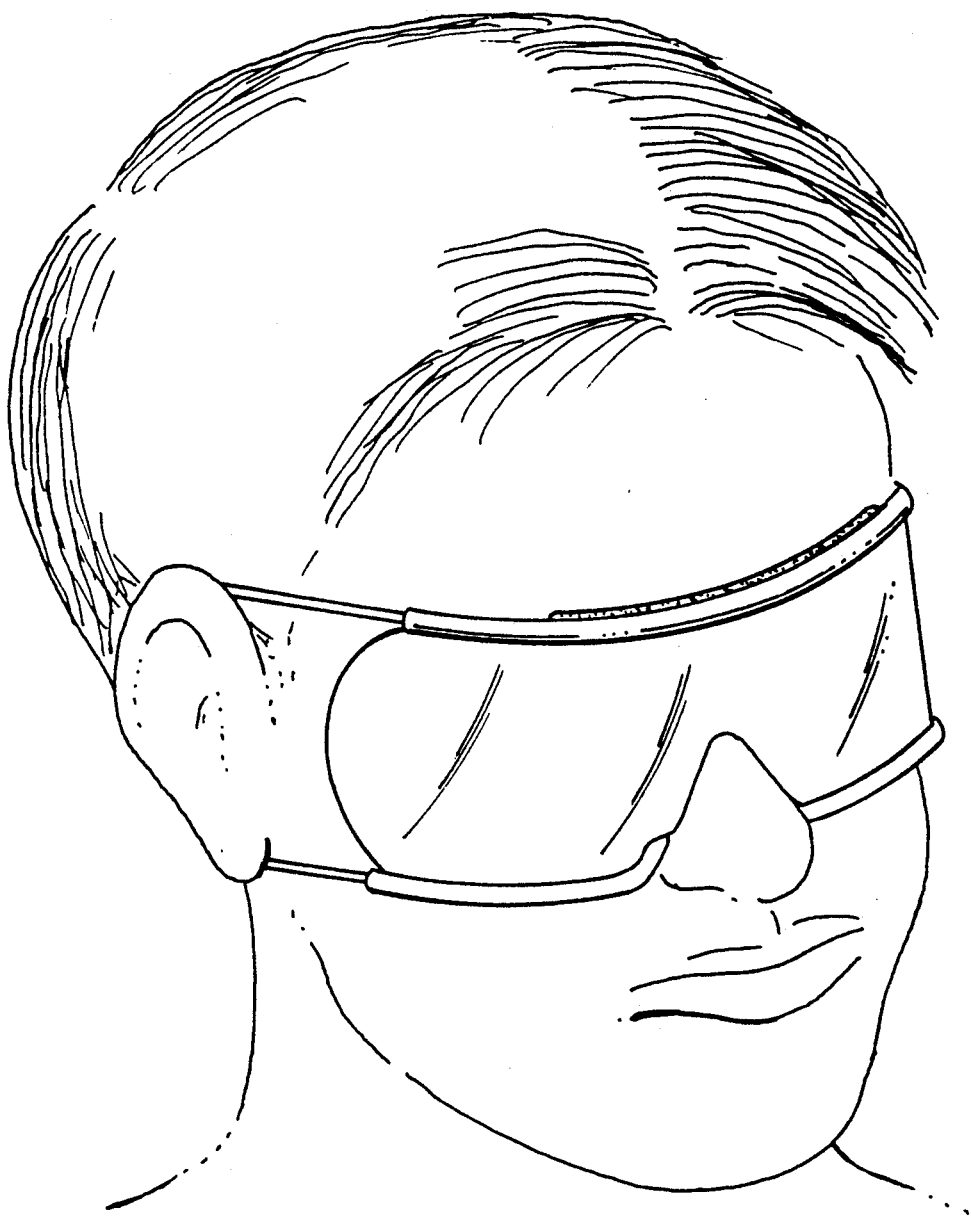
FIG. 7 is a front view of the embodiment of FIG. 1 in place on wearer's face.

FIG. 7 shows the embodiment of FIG. 1 on a wearer's head.

In a separate embodiment, not shown, the ear engaging members can be either modified to include connecting means for attachment around the back of the wearer's head or can be eliminated and the elastic cord 20 will have connecting means for connecting around the back of the wearer's head.

Although only one embodiment of the present invention has been specifically shown above, it should be appreciated that many modifications can be made without departing from the spirit or scope of this invention. Further, it is understood that the subject invention is not intended to be limited by the embodiment set forth above, but shall include modifications and variations that fall within the scope of the attached claims.

What is claimed is:

1. Eyewear having a self-adjusting ear stem system comprising
    a lens member containing at least one lens and having a top edge and a bottom edge, said lens member having a generally inverted U-shaped recess on said bottom edge for mounting said lens member on the nose of a wearer,
    an upper frame member substantially conforming to said top edge of said lens member,
    a lower frame member substantially conforming to said bottom edge of said lens member and containing two inner ends on opposite sides of said recess, and
    an elastic cord moveably connected to said upper and lower frame members and affixed at one or more locations on said upper frame member or said lower frame member, and wherein said elastic cord can be extended on opposite sides of said upper and lower frame members to fit around the ears of a wearer.

2. The eyewear of claim 1 wherein said upper frame member and said lower frame member comprise a hollow tube whereby said elastic cord is disposed there through.

3. The eyewear of claim 2 wherein said elastic cord is affixed to said inner ends of said lower frame member on opposite sides of the wearer's nose.

4. The eyewear of claim 2 wherein said elastic cord is affixed to two piston members, each of said piston members in slideable connection with one of said inner ends of said lower frame member.

5. The eyewear of claim 4 wherein said lower frame member contains a flexible bridge member affixed to said piston members.

6. The eyewear frame of claim 1 wherein said elastic cord consists of an elastomer.

7. The eyewear frame of claim 1 wherein said lens member comprises a single unitary lens.

8. The eyewear frame of claim 7 wherein said lens member is cylindrical.

9. The eyewear frame of claim 7 wherein said lens member is spherical.

10. The eyewear frame of claim 7 wherein said lens member is toroidal.

11. The eyewear frame of claim 1 wherein said elastic cord is attached to an ear engaging member which can fit around the ear of a wearer.

12. The eyewear frame of claim 11 wherein said ear engaging member has substantially an arcuate configuration.

13. The eyewear frame of claim 1 wherein said elastic cord has connecting means for connecting behind a head of the wearer.

14. Eyewear comprising
a lens member having a top edge and a bottom edge having a recess area centrally defined therein to fit over the nose of a wearer,
an upper frame substantially conforming to and connected to said top edge of said lens member comprised of a hollow tube;
two lower frame members comprised of hollow tubes connected to said bottom edge on opposite sides of said recess area and having an inner end adjacent to said recess area and an outer end, said lower frame members substantially conforming to said bottom edge of said lens member;
an elastic cord running through said upper frame member and through said lower frame members and affixed to each of said lower frame members at said inner end; and
two ear engaging members connected to said elastic cord, each of said ear engaging members attached at opposite ends of said elastic cord between said upper frame member and said outer end of each lower frame member, whereby said elastic cord can be extended on opposite sides of the head of a wearer and placed around the ears of the wearer.

15. The eyewear of claim 14 wherein said lens member comprises a single unitary lens.

16. Eyewear comprising
a lens member having a top edge and a bottom edge having a recess area centrally defined therein for mounting said lens member on the nose of a wearer,
an upper frame substantially conforming to and connected to said top edge of said lens member comprised of a hollow tube;
two lower frame members comprised of hollow tubes connected to said bottom edge on opposite sides of said recess area and having an inner end adjacent to said recess area and an outer end, said lower frame members substantially conforming to said bottom edge of said lens member;
an elastic cord running through said upper frame member and through said lower frame members and affixed to two piston members, each of said piston members moveably connected to one of said inner ends of said lower frame members;
a flexible bridge member affixed to said piston members and substantially corresponding to the shape of said recess and whereby said flexible bridge member can move substantially vertically with the movement of said piston members; and
two ear engaging members connected to said elastic cord, each of said ear engaging members attached at opposite ends of said elastic cord between said upper frame member and said outer end of each of said lower frame members, whereby said elastic cord means can be extended on opposite sides of the head of the wearer and placed around the ears of the wearer.

17. The eyewear frame of claim 16 wherein said lens member comprises a single unitary lens.

18. The eyewear frame of claim 17 wherein said unitary lens is cylindrical.

* * * * *